United States Patent [19]

Tanabe et al.

[11] Patent Number: 4,838,879
[45] Date of Patent: Jun. 13, 1989

[54] CATHETER

[75] Inventors: Susumu Tanabe; Masahiro Nudeshima, both of Fujinomiya, Japan

[73] Assignee: Terumo Kabushiki Kaisha, Tokyo, Japan

[21] Appl. No.: 45,601

[22] Filed: May 1, 1987

[30] Foreign Application Priority Data

May 8, 1986 [JP] Japan ................. 61-105744

[51] Int. Cl.⁴ .............................. A61M 25/00
[52] U.S. Cl. ..................... 604/280; 128/658
[58] Field of Search ............. 128/658; 604/117, 280

[56] References Cited

U.S. PATENT DOCUMENTS

| 2,212,334 | 8/1940 | Wallerich | 604/280 |
|---|---|---|---|
| 3,483,859 | 12/1969 | Pittman. | |
| 3,605,750 | 9/1971 | Sheridan et al. | 128/658 |
| 3,885,561 | 5/1975 | Cami | 604/280 |
| 4,279,252 | 7/1981 | Martin | 604/280 |
| 4,469,483 | 9/1984 | Becker et al. | 604/280 |
| 4,571,240 | 2/1986 | Samson et al. | 604/280 |
| 4,581,390 | 4/1986 | Flynn | 604/280 |
| 4,657,024 | 4/1987 | Coneys | 604/280 |
| 4,671,291 | 6/1987 | Wilson | 604/280 |

FOREIGN PATENT DOCUMENTS

| 492021 | 5/1977 | Australia. |
|---|---|---|
| 0033659 | 8/1981 | European Pat. Off.. |
| 0132215 | 1/1985 | European Pat. Off.. |

Primary Examiner—C. Fred Rosenbaum
Assistant Examiner—Kathleen A. Daley
Attorney, Agent, or Firm—Frishauf, Holtz, Goodman & Woodward

[57] ABSTRACT

A catheter having a curved distal end portion or a flexible distal end portion able to bend when being used, which comprises at least one radio opaque ring member provided on the circumference of the catheter, for indicating the direction of the end portion. The radio opaque ring member has an outer diameter approximately equal to that of the catheter, and a width (or a length along the axial direction of the catheter) L which satisfies the following relationship with the magnitude of the inner diameter D of the ring members: $L \leq D\tan(\pi/8)$.

10 Claims, 5 Drawing Sheets

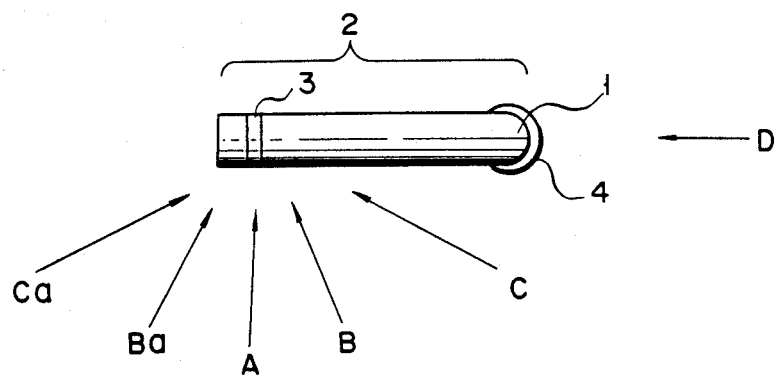
FIG. 3
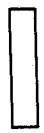 
FIG.4A  FIG.4B
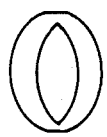 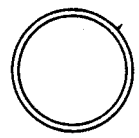
FIG.4C  FIG.4D

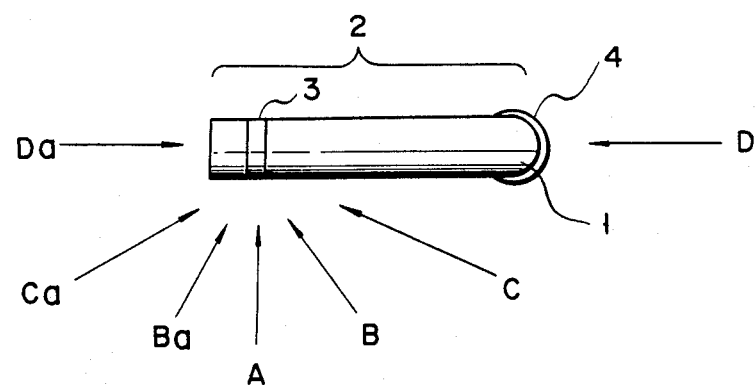
FIG. 8
   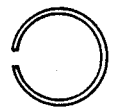
FIG.9A  FIG.9B  FIG.9C  FIG.9D
  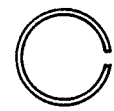
FIG.9E  FIG.9F  FIG.9G

CATHETER

BACKGROUND OF THE INVENTION (a) Field of the Invention

The present invention relates to a catheter having an X-ray contrast medium function.

(b) Description of the Prior Art

Various types of catheters such as an angiographic catheter, a cardiac minute volume measuring catheter, a ureteral catheter, a cholangiographic catheter, bronchographic tube, and a thoracic catheter have been conventionally used for indwelling in body cavities. An X-ray contrast medium is mixed partially or entirely in these catheters, or employed to circumferentially form a ring mark on the outer surface of the catheters. A doctor inserts a catheter having an X-ray contrast medium function into a body cavity while observing an X-ray fluoroscopic image.

The X-ray fluoroscopic image is a two-dimensional type image, so that even if the curved distal end portion of the catheter is twisted in a rotational direction with respect to the proximal axis, or if the catheter itself is deviated toward the rotational direction, the resultant X-ray fluoroscopic image is substantially the same as that obtained along the intended, i.e., the correct direction. The doctor may mistakenly believe that the catheter is directed correctly toward the fluoroscopic plane.

For this reason, when a Judkins type angiographic catheter is inserted in the right coronary artery, with the distal end portion 1a thereof being deviated from right coronary artery port A, as shown in FIG. 1a, the doctor observes the X-ray fluoroscopic image shown in FIG. 1b, and mistakenly believes that he can insert distal end portion 1a into port A. For this reason, insertion operations often have to be repeated, since the catheter sometimes cannot easily be inserted into the location of interest. As a result, the time taken to perform the insertion operation is prolonged and the insertion process causes pain and discomfort to the patient.

SUMMARY OF THE INVENTION

It is an object of the present invention to solve the conventional problem described above and to provide a catheter which allows an operator to easily ascertain whether any twisting of a distal end portion thereof has occurred, on the basis of an X-ray fluoroscopic image, so as to insure that the catheter can be more easily inserted into the location of interest.

In order to achieve the above object of the present invention, a catheter is provided which has a bent distal end portion or a flexible distal end portion able to bend when being used, and has at least one radio opaque (or X-ray shielding) ring member circumferentially formed to cross an axial direction of the catheter, the radio opaque ring member satisfying condition $L \leq D\tan(\pi/8)$ where D is the inner diameter of the radio opaque ring member and L is the length of the radio opaque ring member along the axial direction of the catheter.

The radio opaque ring member is preferably formed in a direction perpendicular to the axial direction of the catheter. In addition, length L is preferably 1 mm or less, and diameter D is preferably 3 mm or less. Moreover, the relationship between inner diameter D and length L of the radio opaque ring member preferably satisfies $L \leq D\tan(\pi/12)$.

A plurality of radio opaque ring members spaced apart from each other may be formed in the distal end portion. Three or more radio opaque ring members spaced apart from each other may be formed in the entire catheter.

The radio opaque ring member may be made of a shape memory alloy, and preferably includes a portion which does not have a radio opaque function. This portion may be in the form of a slit which axially cuts through a ring which is formed around the circumferential surface of the catheter.

The width of the above portion which does not have the X-ray contrast medium function is 1/24 to ¼, and preferably ⅛ to ¼, the entire circumferential length of the ring.

BRIEF DESCRIPTION OF THE DRAWINGS

FIG. 3 is a view of the catheter of FIG. 2, as seen from above;

FIGS. 4-A to 4-D are enlarged views of the X-ray fluoroscopic images of the radio opaque ring member, when viewed from the directions indicated by the arrows in FIG. 3;

FIG. 8 is a view of the catheter of FIG. 7, as seen from above; and

FIGS. 9-A to 9-G are enlarged views of X-ray fluoroscopic images of the radio opaque ring member, when viewed from the directions indicated by the arrows in FIG. 8.

DESCRIPTION OF THE PREFERRED EMBODIMENTS

Figure 1A:
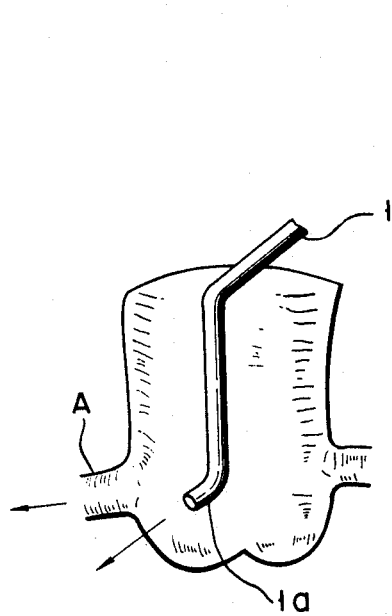
FIG. 1A is a view showing the state of a catheter distal end portion when a conventional catheter is used to perform angiography.
Figure 1B:
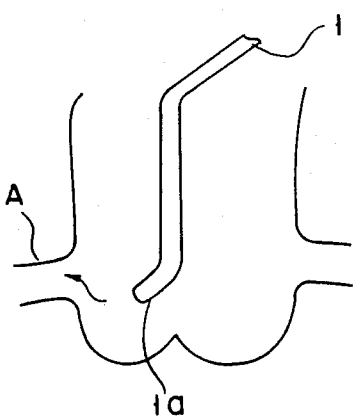
FIG. 1B is a view showing an X-ray fluoroscopic image of FIG. 1.
Figure 2:
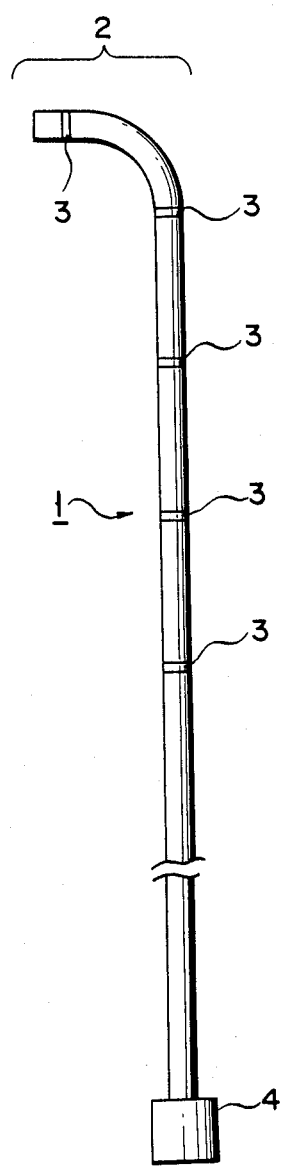
FIG. 2 is a side view of a catheter according to an embodiment of the present invention.

A catheter according to the present invention will be now described, with reference to an embodiment shown in FIG. 2.

Catheter 1 according to this embodiment has curved or flexible distal end portion 2. If distal end portion 2 is flexible, it is able to bend in use. One radio opaque ring member 3 is circumferentially formed in distal end portion 2 so as to cross the axial direction of catheter 1. Radio opaque ring member 3 satisfies condition $L \leq D\tan(\pi/8)$ where L is a length of radio opaque ring member 3 along the axial direction of catheter 1 and D is an inner diameter of radio opaque ring member 3.

Catheter 1 comprises a hollow tube, and connector 4 is connected to the proximal end of catheter 1. In this embodiment, distal end portion 2 is a J-shaped curved portion having a predetermined shape. Distal end portion 2 may have any shape according to various types of operations. In addition, distal end portion 2 may be flexible so as to bend in use.

Various materials can be used for catheter 1. Examples of the catheter material are flexible polyamide, polyurethane, polyethylene, polyester, an ethylenevinyl acetate copolymer, silicone rubber, and polyvinyl chloride. Distal end portion 2 may be formed integrally with the remaining straight portion or may be formed separately from the remaining portion. In the latter case, separate molded members are integrally formed later.

An X-ray contrast medium is preferably mixed in the resin constituting catheter 1. Examples of the X-ray contrast medium are a bismuth compound (e.g., bismuth oxide and bismuth subcarbonate), a barium compound (e.g., barium sulfate), a lead compound (e.g., lead oxide), and a tungsten compound (e.g., tungsten oxide).

Radio opaque ring member 3 is circumferentially formed in distal end portion 2 so as to cross the axial direction of catheter 1. To cross the axial direction of catheter 1 is to form radio opaque ring member 3 at a given angle with respect to the axis of catheter 1. However, radio opaque ring member 3 is preferably perpendicular to the axial direction of catheter 1. In this case, the direction of the distal end of catheter 1 can be distinctly identified. The radio opaque ring member satisfies condition $L \leq D\tan(\pi/8)$ where L is the length of the radio opaque ring member along the axial direction of catheter 1 and D is the inner diameter of the radio opaque ring member. When catheter 1 has distal end portion 2 satisfying the above condition, twisting of distal end portion 2 can be easily known.

Figure 5:
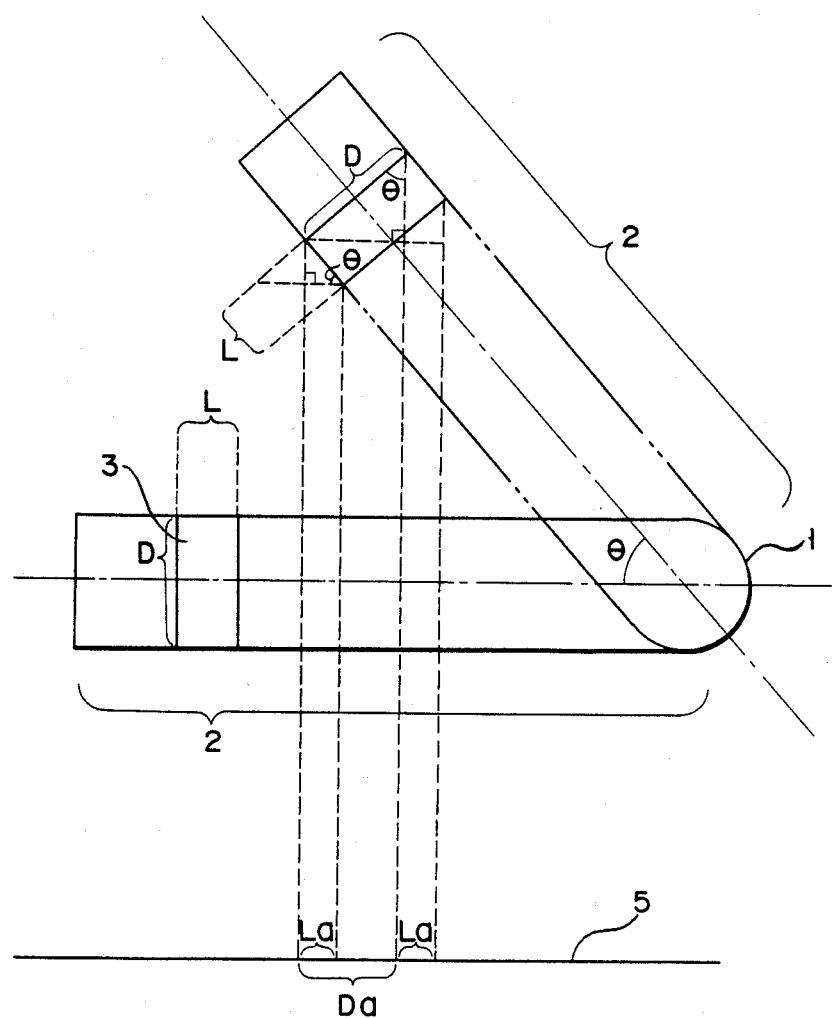
FIG. 5 is a view for explaining a state wherein the catheter distal end portion is parallel to the X-ray fluoroscopic plane, and a state wherein the distal end portion is twisted at angle $\theta$.

Satisfaction of the above condition achieves the object of the present invention, as will be described with reference to FIGS. 3 to 5.

FIG. 3 is a view of catheter 1 of FIG. 2 when viewed from the top. FIG. 4-A is an enlarged view of the X-ray fluoroscopic image of radio opaque ring member 3 when viewed from a direction of arrow A; FIG. 4-B is an enlarged view of the X-ray fluoroscopic image of ring member 3 when viewed from a direction of arrow B or Ba; FIG. 4-C is an enlarged view of the X-ray fluoroscopic image of ring member 3 when viewed from a direction of arrow C or Ca; and FIG. 4-D is an enlarged view of the X-ray fluoroscopic image of ring member 3 when viewed from a direction of arrow D. When radio opaque ring member 3 is observed at a position perpendicular to the axis of catheter 1, ring member 3 is linearly observed. When the radio opaque ring member 3 is observed at a position parallel to the axis of catheter 1, the ring shape can be clearly observed. FIG. 5 is an enlarged view showing a state wherein distal end portion 2 of catheter 1 is parallel to X-ray fluoroscopic plane 5 and a state wherein distal end portion 2 is twisted at angle θ with respect to plane 5. A radio opaque ring member image for L on plane 5 is defined as La and a radio opaque ring member image for D on plane 5 is defined as Da. If Da is larger than La, the image on X-ray fluoroscopic plane 5 represents a ring-like shape and distal end portion 2 is detected not to be parallel to the plane.

La, Da, L, D, and θ has the following relations: La=Lcos θ and Da=Dsinθ. La=Da is established if Lcosθ=Dsinθ. Therefore, $$L = D\tan\theta \qquad (1)$$

Various tests were made by the present inventors and it was found that distal end portion 2 could be guided to a location of interest if θ was less than $\pi/8$ (=22.5 degrees). A substitution of $\theta \leq \pi/8$ into equation (1) yields the following condition:

$$L \leq D\tan(\pi/8) \qquad (2)$$

More specifically, $\tan(\pi/8) = 0.414$, therefore $$L \leq D \times 0.414$$

According to the catheter of the present invention, if distal end portion 2 of catheter 1 is twisted at an angle of 22.5 degrees or more with respect to the X-ray fluoroscopic plane, the resultant fluoroscopic image of radio opaque ring member 3 represents twisting of the distal end portion 2.

The relationship between inner diameter D and length L (along the axial direction of catheter 1) of radio opaque ring member 3 preferably satisfies $L \leq D\tan(\pi/12)$. Since $\pi/12$ is 15 degrees, even slight twisting can be visually discriminated.

More specifically, if the inner diameter of radio opaque ring member 3 is about 3 mm, length L of radio opaque ring member 3 along the axial direction of catheter 1 is preferably 1 mm or less and more preferably 0.1 to 1 mm.

A plurality of radio opaque ring members 3 are preferably formed excluding the one formed in distal end portion 2, as shown in FIG. 2. In this case, if a distance between the adjacent radio opaque ring members is determined, a magnification of the X-ray fluoroscopic image can be known by this distance.

Figure 6:
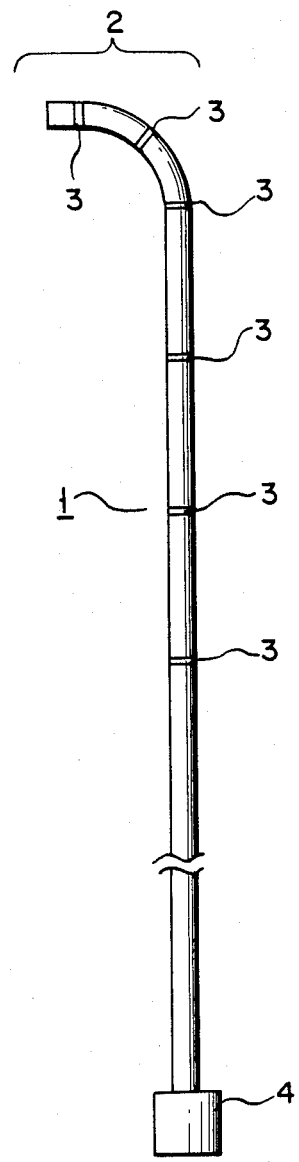
FIG. 6 is a side view of a catheter according to another embodiment of the present invention.

Furthermore, a plurality of radio opaque ring members 3 may be formed in distal end portion 2. As shown in FIG. 6, two radio opaque ring members spaced apart from each other are formed in distal end portion 2. The reference numerals as in FIG. 2 denote the same parts in FIG. 6, and a detailed description thereof will be omitted.

Since radio opaque ring member 3 has only the X-ray contrast medium function, it may be made of a metal or formed by metal deposition or printing of a paint or the like containing a contrast medium. Preferably, a material having a good X-ray contrast medium function is used. In particular, if catheter 1 is made of a material mixed with an X-ray contrast medium, the material for the radio opaque ring member must have better X-ray contrast medium function. For this reason, radio opaque ring member 3 is preferably made of stainless steel, gold, a titanium-nickel alloy or the like.

Radio opaque ring member 3 is preferably fitted on the outer surface of catheter 1 so as to have substantially the same outer diameter as that of catheter 1 without forming a step therebetween.

In order to mount the radio opaque ring member in the manner described above, the radio opaque ring member can be embedded in the wall of catheter 1. Alternatively, an annular groove is formed on the outer surface of catheter 1, and an radio opaque ring member is fitted in the groove. Furthermore, in order to smoothen the outer surface, a plastic coating can be formed thereon. In a preferable method, a shape memory alloy is used as a material of the radio opaque ring member and is wound around the catheter 1 to memorize the circumferential shape thereof. Thereafter, the shape memory alloy is straightened and is fitted in an annular groove formed on the outer surface of catheter 1. In this state, the memory shape alloy is heated or cooled to restore the memorized shape, thereby easily mounting the radio opaque ring member on catheter 1. The annular groove need not be formed on the outer surface of catheter 1. In this case, the memory shape alloy is heated and the corresponding portion of the catheter is also heated to embed the alloy in the wall of catheter 1. Various types of shape memory alloys may be used, and a typical example is a titanium-nickel alloy.

A catheter according to another embodiment of the present invention will be described with reference to FIGS. 7 to 9.

Catheter 1 according to this embodiment has curved or flexible distal end portion 2. If distal end portion 2 is flexible, it is bent in use. One radio opaque ring member 3 is circumferentially formed in distal end portion 2 so as to cross the axial direction of catheter 1. Radio opaque ring member 3 satisfies condition $L \leq D\tan(\pi/8)$ where L is a length of radio opaque ring member 3 along the axial direction of catheter 1 and D is an inner diameter of radio opaque ring member 3.

Portion 6 having no X-ray contrast medium function is formed in radio opaque ring member 3 and extends along the axial direction of catheter 1 at a portion substantially perpendicular to the surface formed by bending distal end portion 2.

In this catheter, other radio opaque ring member portions excluding portion 6 are the same as those in the above embodiment. Therefore, only portion 6 will be described below.

Portion 6 having no X-ray contrast medium function extends along the axial direction of catheter 1 in a narrow strip-like shape but need not be parallel to the axis of catheter 1. Portion 6 may be inclined at a given angle with respect to the axis of catheter 1. It is thus essential for portion 6 to cross the main body of radio opaque ring member 3. Preferably, the radio opaque ring member is perpendicular to the axial direction of catheter 1 and the portion having no X-ray contrast medium function is parallel to the axis of catheter 1.

The portion having no X-ray contrast medium function may have any form. For example, this portion may be slit 6 formed in radio opaque ring member 3 or a member having no X-ray contrast medium function and connecting both ends of ring member 3.

The width of portion 6 having no X-ray contrast medium function is preferably 1/24 to ¼, more preferably ⅛ to ¼ the overall circumferential length of radio opaque ring member 3. Within this range, X-ray fluoroscopic images of ring member 3 are not adversely affected. Therefore, the portion having no X-ray contrast medium function can be clearly identified in the X-ray fluoroscopic images.

X-ray distal end portion images of the catheter having a portion with no X-ray contrast medium function will be described with reference to FIGS. 8 and 9.

Figure 7:
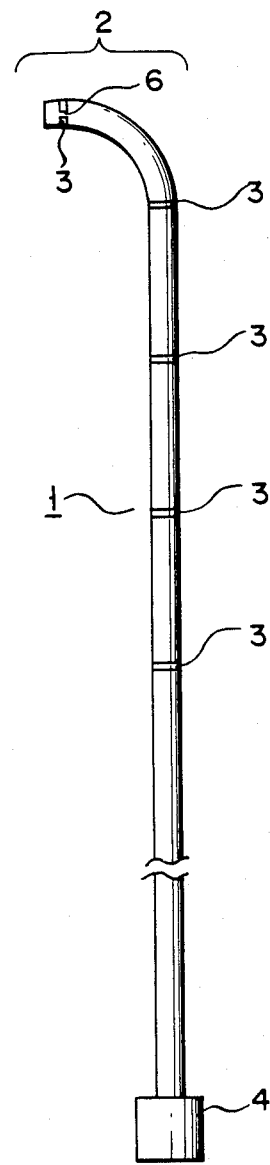
FIG. 7 is a side view of a catheter according to yet another embodiment of the present invention.

FIG. 8 is a view of the catheter of FIG. 7 when viewed from the top thereof. FIG. 9-A shows an enlarged X-ray fluoroscopic image of ring member 3 when viewed from a direction of arrow A; FIG. 9-B shows an enlarged X-ray fluoroscopic image thereof when viewed from a direction of arrow B; FIG. 9-E shows an enlarged X-ray fluoroscopic image thereof when viewed from a direction of arrow Ba; FIG. 9-C shows an enlarged X-ray fluoroscopic image thereof when viewed from a direction of arrow C; FIG. 9-F shows an enlarged X-ray fluoroscopic image thereof when viewed from a direction of arrow Ca; FIG. 9-D shows an enlarged X-ray fluoroscopic image thereof when viewed from a direction of arrow D; and FIG. 9-G shows an enlarged X-ray fluoroscopic image thereof when viewed from a direction of arrow Da.

As can be apparent from the above figures, when the radio opaque ring member is observed at a position perpendicular to the axis of catheter 1, the ring member is linearly observed. However, when the viewing position is changed to that parallel to the axis of catheter 1, the ring member can be clearly observed as a ring-like shape. At the same time, the position of the portion having no radio opaque ring member is changed depending on the viewing positions. Therefore, the doctor can visually observe that distal end portion 2 of catheter 1 is deviated on the X-ray fluoroscopic plane side or the opposite side with respect to the axis of catheter 1.

The catheter according to the present invention can be used as an angiographic catheter for the abdomen, brain, heart, coronary artery and the like, a cardiac minute volume measuring catheter, a monitoring catheter (e.g., a blood pressure measuring catheter used near a heart), and an obturator or vasodilator therapeutic catheter as well as a catheter as a ureteral catheter, a cholangiographic catheter, abdominal catheter, or a bronchographic catheter.

The catheters of the present invention, e.g., the angiographic catheters shown in FIGS. 2, 6, and 7 can be used in the same manner as in the conventional catheter. For example, the curved distal end portion is straightened by a guide wire inserted in the catheter and is inserted in a femoral artery. When the catheter passes by an aortic arch, the guide wire is removed. The distal end of the catheter is turned through 180 degrees in a valsalva cavity and is inserted in the right coronary artery port. At the same time, the doctor checks the position of the catheter while observing the corresponding X-ray fluoroscopic image. The catheter is thus indwelled in the correct position. In particular, according to the catheter of the present invention, even if the distal end portion of the catheter is slightly deviated from the X-ray fluoroscopic plane, such a deviation can be checked since the radio opaque ring member provides a ring-like image. The doctor turns the catheter located outside the femoral artery such that the X-ray fluoroscopic image of the radio opaque ring member becomes linear. The distal end portion is set parallel to the X-ray fluoroscopic plane and the distal end portion is inserted in the right coronary artery port. Thereafter, an X-ray contrast medium is injected from the rear end portion of the catheter, thereby performing angiography.

The present invention will be described in detail by way of its examples.

EXAMPLE 1

Judkins type right coronary artery angiographic catheter 7Fr (outer diameter: 2.3 mm) with a curved distal end portion having a length of 5 to 10 mm was prepared. In this catheter, stainless radio opaque ring members each having an inner diameter of 2.13 mm, an outer diameter of 2.33 mm, and a width (i.e., the length along the axial direction of the catheter) of 0.88 mm were formed on the outer circumferential surface portions at 1-, 21-, 41-, and 81-mm positions away from the distal end.

The resultant catheter was inserted into the femoral artery and the aortic arch. The catheter was then rotated through 180 degrees in the valsalva cavity, and the distal end portion of the catheter was inserted in the right coronary artery. In this operation, the positional relationship between the X-ray fluoroscopic plane and the distal end portion of the catheter could be appropriately identified by the X-ray fluoroscopic image of the radio opaque ring members. Therefore, the distal end of the catheter could be accurately inserted in the right coronary artery port. By measuring a distance between the radio opaque ring members in the straight portion of the catheter with reference to the X-ray fluoroscopic image, a magnification of the X-ray fluoroscopic image could be accurately measured, and hence the diameter of the blood vessel could be measured. By using a pigtail catheter prepared as in the catheter, the size of the left ventricle of the heart could be accurately measured.

EXAMPLE 2

Sones type angiographic catheter 7Fr (outer diameter: 2.3 mm) was prepared. Radio opaque ring members made of a shape memory alloy (titanium-nickel alloy) were straightened and mounted on the outer surface of catheter at 1-, 21-, 41-, and 81-mm positions away from the distal end of the catheter. Each radio opaque ring member had a 0.5-mm wide slit, an inner diameter of 2.13 mm, an outer diameter of 2.33 mm, and a width (length along the axial direction of the catheter) of 0.88 mm.

Hot air was blown to the set portions to soften the catheter material, and at the same time the radio opaque ring members restored the memorized shape and were embedded in the wall of the catheter.

The resultant catheter was inserted in the left coronary artery and the left ventricle of the heart under the fluoroscopic observation.

The distal end portion of the catheter could be stereographically observed, and the forward or reverse rotational direction of the distal end portion could be identified according to the position of the slit, thus achieving easy indwelling.

By measuring a distance between the radio opaque ring members of the linear catheter portion in the X-ray fluoroscopic image, the magnification of the X-ray fluoroscopic image could be accurately measured. As a result, the size of the left ventricle could be accurately measured.

In the catheter having the curved distal end portion or the flexible distal end portion to be curved in use, at least one radio opaque ring member is mounted on the catheter so as to cross the axial direction of the catheter. In addition, inner diameter D and length L of the radio opaque ring member satisfy condition $L \leq D\tan(\pi/8)$. If the distal end portion of the catheter is twisted at an angle exceeding 22.5 degrees with respect to the X-ray fluoroscopic plane, the X-ray fluoroscopic image of the radio opaque ring member represents a ring-like shape, thereby allowing the operator to easily identify twisting of the distal end portion of the catheter and to easily correct such twisting. Therefore, the catheter can be easily indwelled in the location of interest.

When the radio opaque ring member is arranged perpendicular to the axial direction of the catheter, the direction of the distal end of the catheter can be identified.

In the catheter having the curved distal end portion or the flexible distal end portion to be curved in use, at least one radio opaque ring member is mounted on the outer surface of the distal end portion so as to cross the axial direction of the catheter. At the same time, inner diameter D and length L of the radio opaque ring member satisfy condition $L \leq D\tan(\pi/8)$. In addition, this radio opaque ring member has a portion having no X-ray contrast medium function and extending along the axial direction of the catheter. If the distal end portion of the catheter is twisted at an angle exceeding 22.5 degrees with respect to the X-ray fluoroscopic plane, the X-ray fluoroscopic image represents a ring-like image of the radio opaque ring member. In addition, the forward or reverse rotational direction of the distal end with respect to the axis of the catheter can be identified, and thus twisting of the distal end portion can be easily corrected. If the width of the portion having no X-ray contrast medium function falls within the range of 1/24 to ¼ the overall circumferential length of the radio opaque ring member, the portion having no X-ray contrast medium function can be easily recognized in the X-ray fluoroscopic image thereof.

What is claimed is:

1. A catheter having one of a curved distal end portion and a flexible distal end portion able to bend when being used, comprising at least one radio opaque ring member circumferentially formed on said catheter, so as to cross an axial direction of said catheter, said radio opaque ring member satisfying the condition:

$$L \leq D\tan(\pi/8)$$

where D is the inner diameter of said radio opaque ring member and L is the length thereof along the axial direction of said catheter, said radio opaque ring member being provided with a slit-shaped portion having substantially no radio opaque function and extending along the axial direction of said catheter whereby said radio opaque ring member with it's slit-shaped portion enables determination of the inclining direction of said catheter.

2. A catheter according to claim 1, wherein said slip-shaped portion has a width which falls within a range of 1/24 to ¼ an overall circumferential length of said radio opaque ring member.

3. A catheter according to claim 1, wherein said radio opaque ring member is perpendicular to the axial direction of said catheter.

4. A catheter according to claim 1, wherein the length L of said radio opaque ring member along the axial direction of said catheter is not more than 1 mm.

5. A catheter according to claim 1, wherein the inner diameter D of said radio opaque ring member is not more than 3 mm.

6. A catheter according to claim 1, wherein said radio opaque ring member satisfies the condition:

$$L \leq D\tan(\pi/12).$$

7. A catheter according to claim 1, wherein said radio opaque ring member comprises a plurality of members spaced apart from each other and formed on said distal end portion.

8. A catheter according to claim 1, wherein said radio opaque ring member comprises at least three members which are equidistantly formed along the axial direction of said catheter.

9. A catheter according to claim 1, wherein said radio opaque ring member comprises a shape memory alloy.

10. A catheter according to claim 1, wherein said catheter is an angiographic catheter.

* * * * *

UNITED STATES PATENT AND TRADEMARK OFFICE
CERTIFICATE OF CORRECTION

PATENT NO. : 4,838,879

DATED : June 13, 1989

INVENTOR(S) : TANABE et al

It is certified that error appears in the above-identified patent and that said Letters Patent is hereby corrected as shown below:

Column 8, line 1 (claim 2), "slip" should read --slit--.

Signed and Sealed this

Twenty-seventh Day of November, 1990

Attest:

HARRY F. MANBECK, JR.

*Attesting Officer*  *Commissioner of Patents and Trademarks*